(12) United States Patent
Terrasse et al.

(10) Patent No.: US 10,624,884 B2
(45) Date of Patent: Apr. 21, 2020

(54) H4 AGONIST MOLECULE FOR THE TREATMENT OF IDIOPATHIC PULMONARY FIBROSIS

(71) Applicant: H4 ORPHAN PHARMA, Dijon (FR)

(72) Inventors: Gaëtan Terrasse, Saint Vallier (FR); Catherine Bur, Orgerus (FR)

(73) Assignee: H4 ORPHAN PHARMA, Dijon (FR)

( * ) Notice: Subject to any disclaimer, the term of this patent is extended or adjusted under 35 U.S.C. 154(b) by 0 days.

(21) Appl. No.: 16/401,423

(22) Filed: May 2, 2019

(65) Prior Publication Data

US 2019/0321352 A1 Oct. 24, 2019

Related U.S. Application Data

(63) Continuation of application No. 16/083,624, filed as application No. PCT/EP2017/056434 on Mar. 17, 2017, now abandoned.

(60) Provisional application No. 62/310,033, filed on Mar. 18, 2016.

(30) Foreign Application Priority Data

Mar. 18, 2016 (FR) ..................... 16 52332

(51) Int. Cl.
| | | |
|---|---|---|
| *A61K 31/4741* | (2006.01) | |
| *A61K 9/00* | (2006.01) | |
| *A61K 9/48* | (2006.01) | |
| *A61K 9/20* | (2006.01) | |
| *A61K 9/28* | (2006.01) | |
| *A61P 11/00* | (2006.01) | |

(52) U.S. Cl.
CPC ........ *A61K 31/4741* (2013.01); *A61K 9/0053* (2013.01); *A61K 9/20* (2013.01); *A61K 9/28* (2013.01); *A61K 9/48* (2013.01); *A61P 11/00* (2018.01)

(58) Field of Classification Search
CPC .............................. A61K 31/4741; A61P 11/00
See application file for complete search history.

(56) References Cited

U.S. PATENT DOCUMENTS

| | | | |
|---|---|---|---|
| 7,048,928 B2 | 5/2006 | Loria et al. | |
| 7,927,600 B2 | 4/2011 | Loria et al. | |
| 8,207,188 B2 | 6/2012 | Nicolaou et al. | |
| 8,207,292 B2 | 6/2012 | Nicolaou et al. | |
| 2010/0144718 A1 | 6/2010 | Nicolaou et al. | |
| 2013/0303565 A1* | 11/2013 | Terrasse ............ | C07D 491/056 514/291 |

FOREIGN PATENT DOCUMENTS

| | | |
|---|---|---|
| EP | 2 659 890 A1 | 11/2013 |
| FR | 1295309 A | 6/1962 |
| WO | 2006/100392 A1 | 9/2006 |
| WO | 2006/131737 A2 | 12/2006 |
| WO | 2008/006974 A2 | 1/2008 |
| WO | 2009/155611 A1 | 12/2009 |

OTHER PUBLICATIONS

Richard H. Gomer, "New Approaches to Modulating Idiopathic Pulmonary Fibrosis", Curr Allergy Asthma Rep., 2013, p. 607-612, vol. 13; 9 pgs.
International Search Report with English translation and Written Opinion of the International Search Authority dated May 9, 2017 of corresponding International application No. PCT/EP2017/056434; 12 pgs.
Rosa et al. The Journal of Pharmacology and Experimental Therapeutics, Nov. 2014, vol. 351, pp. 308-316 (Year: 2014).
Lucarini et al. Pharmacological Research, 2016, vol. 111, pp. 740-748 (Year: 2016).

* cited by examiner

*Primary Examiner* — James D. Anderson
(74) *Attorney, Agent, or Firm* — Maier & Maier, PLLC

(57) ABSTRACT

The present invention concerns the use of an H4 agonist molecule against histamin, enantiomers of (AMINO-7 TRI-ETHOXY-4,5,6 OXO-1 DIHYDRO-1,3 ISOBENZO-FURANNYL-3)-1 METHOXY-8 METHYL-2 METHYL-ENEDIOXY-6,7 TETRAHYDRO-,2,3,4 ISOQUINOLINE or tritoqualine, for the treatment of idiopathic pulmonary fibrosis.

4 Claims, 5 Drawing Sheets

H4 AGONIST MOLECULE FOR THE TREATMENT OF IDIOPATHIC PULMONARY FIBROSIS

CROSS-REFERENCE TO RELATED APPLICATIONS

This application is a continuation of U.S. patent application Ser. No. 16/083,624, filed Sep. 10, 2018, which is a national phase of International Application No. PCT/EP2017/056434, filed Mar. 17, 2017, which claims benefit of U.S. Provisional Patent Application No. 62/310,033, filed Mar. 18, 2016, which claims priority to French Patent Application No. 1652332, filed Mar. 18, 2016, the entire contents of which are incorporated herein by reference.

FIELD

This invention relates to the use of chemical substances the laevorotatory and dextrorotatory enantiomers of (AMINO-7 TRIETHOXY-4,5,6 OXO-1 DIHYDRO-1,3 ISOBENZOFURANNYL-3)-1 METHOXY-8 METHYL-2METHYLENEDIOXY-6,7 TETRAHYDRO-,2,3,4 ISOQUINOLINE or tritoqualine for treating idiopathic pulmonary fibrosis.

BACKGROUND

Idiopathic pulmonary fibrosis (IPF) is one of the 200 pulmonary diseases in the family of interstitial lung diseases, which affect the pulmonary interstitium, the tissue located between the alveolar spaced of the lungs.

Idiopathic pulmonary fibrosis is an idiopathic interstitial lung disease, which is in turn an interstitial lung disease, also known as diffuse parenchymatous lung disease.

Idiopathic pulmonary fibrosis is a rare disease (prevalence of about 13 to 20 cases/100,000 habitants) that belongs to the group of idiopathic diffuse interstitial lung disease with chronic evolution, of which it is the most frequent form (60% of cases) and the most severe.

Idiopathic diffuse interstitial lung disease occurs in the absence of an identified specific cause or context, in opposition to interstitial diffuse lung diseases of which the medical cause is known (interstitial lung diseases induced by drugs or pneumoconiosis for example).

Idiopathic pulmonary fibrosis was defined recently in the framework of an international consensus classification. The term idiopathic pulmonary fibrosis beforehand encompassed several entities which are now very distinct, and in particular non-specific interstitial lung disease which has been recognised as an anatomoclinical entity in the group of idiopathic diffuse interstitial lung diseases.

The definition of idiopathic pulmonary fibrosis is now limited to the cases of idiopathic diffuse interstitial lung diseases where the lung biopsy shows a histopathological aspect of interstitial lung disease commune (usual interstitial pneumonia).

Characteristic computed tomography anomalies and a respiratory functional effect are also required in order to retain the diagnosis of idiopathic pulmonary fibrosis. The diagnosis is based on an anatomo-radio-clinical summary.

Idiopathic pulmonary fibrosis starts between 60 and 70 years with a slight male predominance. It is rare before the age of 50 years.

The disease evolves progressively to chronic respiratory failure and death, with a median survival time of about 3 years, and survival at 10 years of about only 10%.

The disease is revealed by a dyspnea exertional with progressive installation, a non-productive cough, and more rarely general signs. During examination, bilateral dry crackling sounds of the bases (reproduction the sound of "Velcro") are constant.

Nail clubbing is present in nearly half of the cases. Cyanosis and signs of right ventricular failure are observed only at an advanced stage of the disease.

The diagnosis is often made late, at a stage where the functional and computed tomography anomalies are already marked. The chest roentgenogram shows predominant peripheral reticular opacities clearly in the bases, and a reduction in the lung volume.

Millimetric-slice chest computerized tomography is the essential examination of the diagnosis: the characteristic aspect shows reticular opacities of the bases producing a pseudocystic subpleural honeycomb aspect, traction bronchiectasis, and signs of distortion of the pulmonary parenchyma, with little ground-glass opacities; Pulmonary function testing shows a restrictive ventilatory disorder (decrease in the vital capacity and in the total lung capacity). There is also a functional disorder of the alveolar-capillary membrane demonstrated by a decrease in the carbon monoxide (CO) transfer factor and coefficient. Hypoxemia is often absent at rest, but it appears during exercise; exercise hypoxemia is sometimes the only respiratory functional abnormality initially.

Patients who have an idiopathic pulmonary fibrosis also have an increased risk of bronchial cancer.

If the overall prognosis of the disease is bad, there are substantial inter-individual differences. Several recent studies have made it possible to identify prognostic factors:

- Deterioration of respiratory function during the months following diagnosis is a pejorative factor. As such, a decrease in the forced vital capacity of 10% or more in 6 months, or in the CO diffusion capacity of 15% or more in 12 months, is an independent predictive factor of a high risk of death.
- The existence of a saturation less than 88% during a 6-minute treadmill test is a predictive factor of a bad prognosis.
- The occurrence of pulmonary hypertension during the evolution is also a bad prognosis.
- The substantial alteration in the CO transfer factor.
- The extent of the honeycomb lesions with chest computerized tomography, and the number of fibroblast outbreaks on the lung biopsy.

The treatment for idiopathic pulmonary fibrosis aims to increase the life expectancy, the respiratory function, the quality of life, and to prevent the risk of acute exacerbation of the disease.

No treatment has, to date, demonstrated its efficacy in improving survival in this disease. There is no curative treatment to date. In patients where the disease is aggravating and reaching severe stages, oxygen therapy and lung transplantation are the recommended treatments, according to the French National Authority for Health (HAS).

Two drugs have however obtained a Marketing Authorisation:

- On the one hand, pirfenidone (Esbriet) of which the results on survival are of little or no significance. The mode of action of pirfenidone is not known. Pirfenidone is indicated in the treatment of slight to moderate IPF. This product is used at very high doses around 2.4 grams/day.

According to HAS (French National Authority for Health), the efficacy of pirfenidone was appreciated according to an intermediate criterion evaluating the pulmonary function and marker of the progression of the disease. The difference observed on this criterion is in favour of pirfenidone in relation to a placebo but this difference is low, the clinical significance is not well known and is heterogeneous from one study to another.

The effect observed with ESBRIET on the decline of the pulmonary function in patients with precise functional criteria (FVC≥50% and DLCo≥35%) is low. The clinical benefit brought to patients afflicted with idiopathic pulmonary fibrosis is difficult to appreciate as the clinically pertinent criteria (quality of life, overall survival, etc.) underwent exploratory and non-robust analyses. However, consolidation studies of patients have made it possible to reveal on certain patient profiles a notable improvement in survival.

The main adverse reactions of pirfenidone observed were gastrointestinal disorders (nausea, diarrhoea, dyspepsia), skin disorders (photosensitisation and rash) and metabolism and nutrition disorders (anorexia and loss of appetite).

On the other hand, nintedanib known under the commercial name of OFEV was approved recently in the USA for the treatment of idiopathic pulmonary fibrosis. It has also received a favourable opinion from the CHMP of the European Medicines Agency (EMA) and is on hold for Marketing Authorisation at the European level. The mode of action of nintedanib is that of a tyrosine kinase inhibitor. This product is used at the dose of 200 to 400 mg/day. Many side effects have been observed, in particular gastrointestinal side effects.

The French National Authority for Health considers that the following are not recommended (absence of an acceptable methodology of study, absence of demonstration on criteria for functional judgement): corticoids as monotherapy, colchicine, cyclosporine A, interferon γ1b, bosentan, etanercept, corticoid/immunomodulator association and the acetylcysteine/prednisone/azathioprine tritherapy.

An oxidant-antioxidant imbalance was revealed during idiopathic pulmonary fibrosis. The N-acetylcysteine (precursor of glutathione, one of the main antioxidants in the lung), was evaluated as a treatment for idiopathic pulmonary fibrosis.

A randomized controlled trial with N-acetylcysteine (1,800 mg/d for one year) [in addition to a treatment with corticoids and azathioprine] has recently shown a modest respiratory functional benefit with an average decrease in the decline of the forced vital capacity of 0.18 L (0.03-0.32) which is a relative difference of 9%, and of the diffusion of CO of 24% but there was no difference in mortality between the two groups.

The French National Authority for Health considers that acetylcysteine, having shown a slowing down in the deterioration in the vital capacity with a low level of evidence, can be administered to certain patients. This product does not have a Marketing Authorisation to date.

Many products are currently being studied for the treatment of idiopathic pulmonary fibrosis:

Monoclonal antibodies (lebrikizumab in phase II and tralokinumab in phase III) of which the status in 2015 is uncertain.

BMS-986202 (Lysophosphatidic Acid Receptor Antagonist) developed by Bristol-Myers-Squibb is currently in phase II.

More than 154 studies are underway but few products currently get through phase II, because the results are particularly mediocre.

As such idiopathic pulmonary fibrosis is currently a pathology with few commercially available treatments that are really effective (only ESBRIET to date in the slight and moderate IPFs).

Tritoqualine is a chemical substance known for many years now, and used as an antihistamine. Its manufacture is described in French patent 1.295.309.

Tritoqualine is 7-Amino-4,5,6-triethoxy-3-(5,6,7,8-tetrahydo-4-methoxy-6-methyl-1,3-dioxolo[4,5-g]isoquinolin-5-yl) phthalide. In its marketed pharmaceutical form, it has the form of a mixture of enantiomers.

Tritoqualine is known for its anti-allergic activity through its inhibiting action on histidine decarboxylase. This activity is however very low and does not explain the many properties that it has on varied clinical symptoms, rhinitis, hives, eczema, mastocytosis.

One of the inventors with other inventors has demonstrated that tritoqualine had a very substantial action on a new receptor, the histamine H4 receptor.

This activity of tritoqualine on the H4 receptor was demonstrated in a patent US 2010144718A "TREATMENT OF DISEASES MODULATED BY A H4 RECEPTOR AGONIST" Gaëtan Terrasse and coll.

This patent does not however describe the activity of tritoqualine on Idiopathic pulmonary fibrosis.

Another patent WO2008006974A2 on H4 agonists describes the use of these products in the protection of haematopoietic precursors in the framework of chemotherapy.

This latter patent and no other scientific document reveals the action of H4 agonists to histamine on Idiopathic pulmonary fibrosis.

Commercial tritoqualine has the form of a white powder, highly sensitive to light which degrades it in Cotarnine and phthalic acid.

Commercial tritoqualine (called Hypostamine) is in tablet form with a concentration of 100 mg per tablet.

Tritoqualine has 2 asymmetric carbons, but the commercial form is a mixture of 2 enantiomers (R—R and S—S).

The inventors have revealed the surprising properties of tritoqualine in the conventional animal model of idiopathic pulmonary fibrosis, that of the bleomycin mouse model.

Figure 3A:
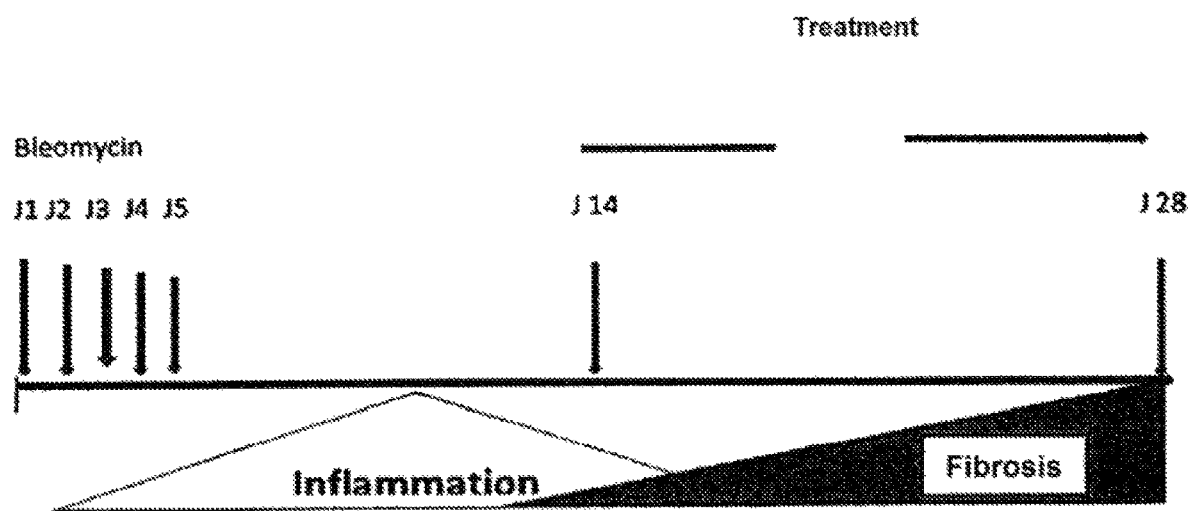

FIG. 3A explains the protocol used. The bleomycin is inhaled for 5 days in order to provoke pulmonary fibrosis. Starting on D14 tritoqualine is administered orally every day until D28.

The doses used in this model are 20 and 40 mg/kg which is approximately the dose in an adult male of 70 kg of 1.4 g/day to 2.8 g/day.

Figure 1A:
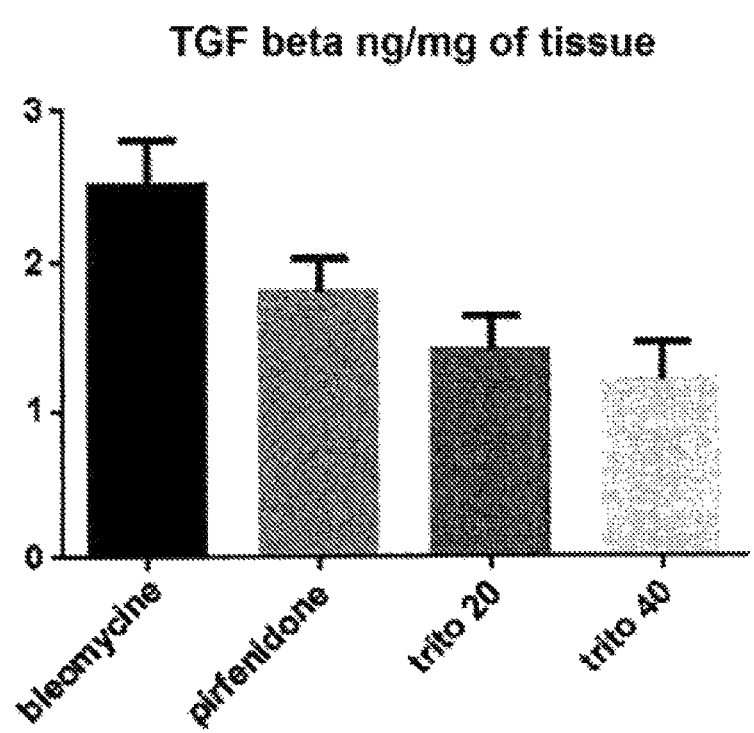

FIG. 1A shows the therapeutic effect of tritoqualine on the secretion of TGF beta expressed in ng/mg of tissue.

Figure 2A:
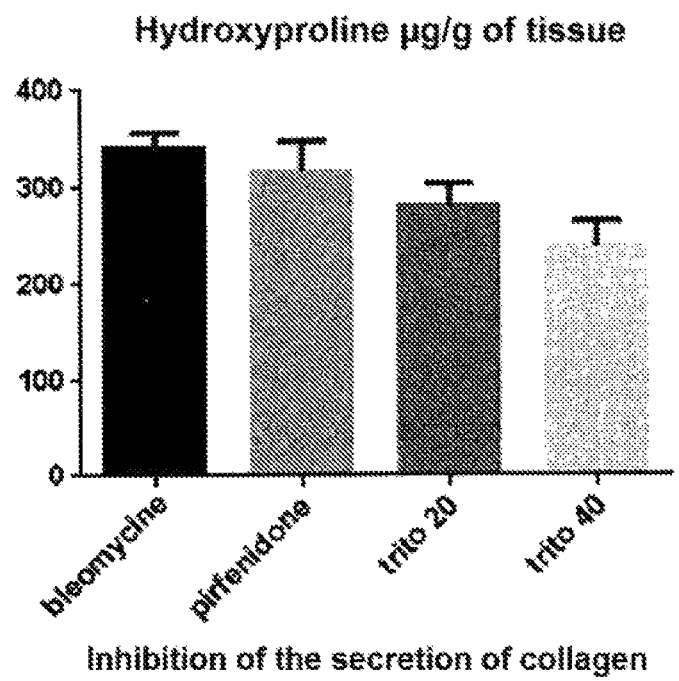

FIG. 2A shows the effect of tritoqualine on the secretion of collagen with pirfenidone as a control.

Figure 2B:
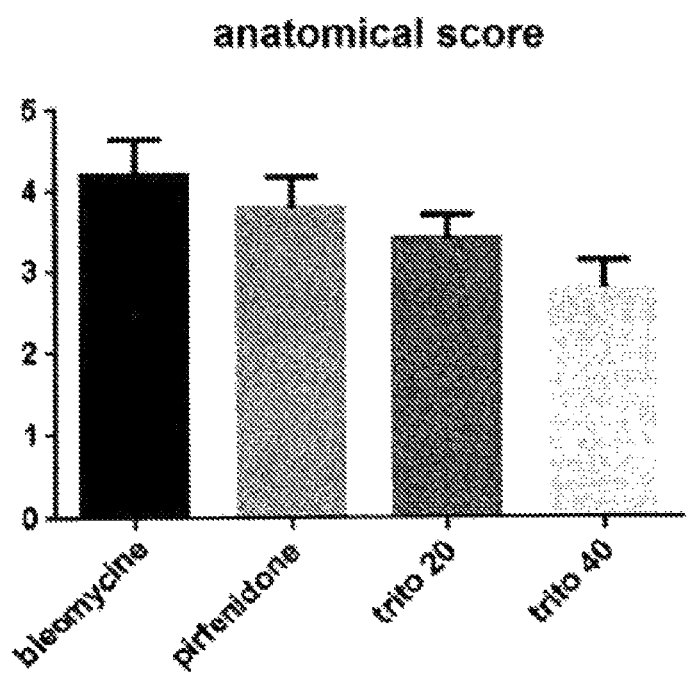

FIG. 2B shows the therapeutic effect of tritoqualine on the anatomical score with pirfenidone as a control.

Figure 3B:
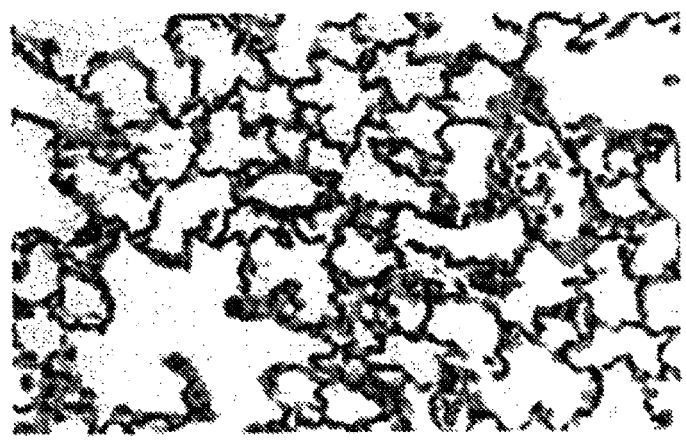
Figure 4A:
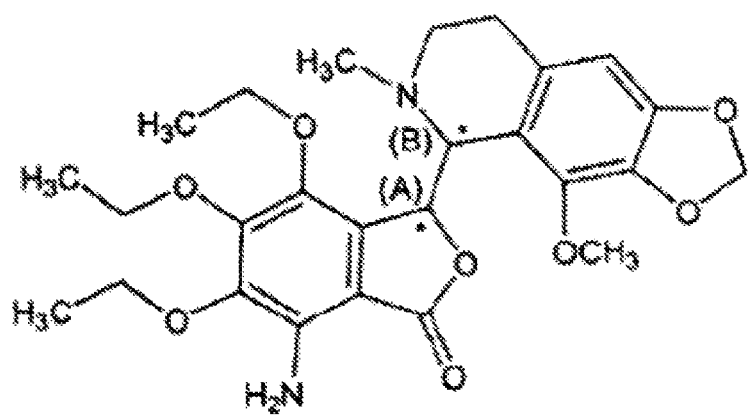
FIG. 4A shows the present of asymmetric carbons, which are noted as A and B.
Figure 4B:
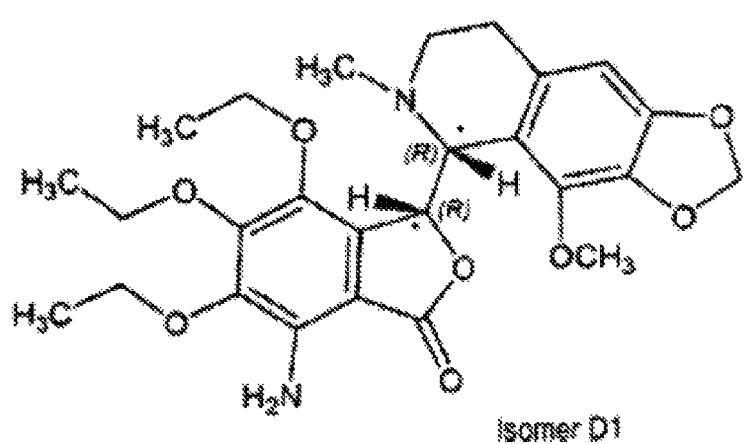
FIG. 4B shows the form of the isomer D1.
Figure 4C:
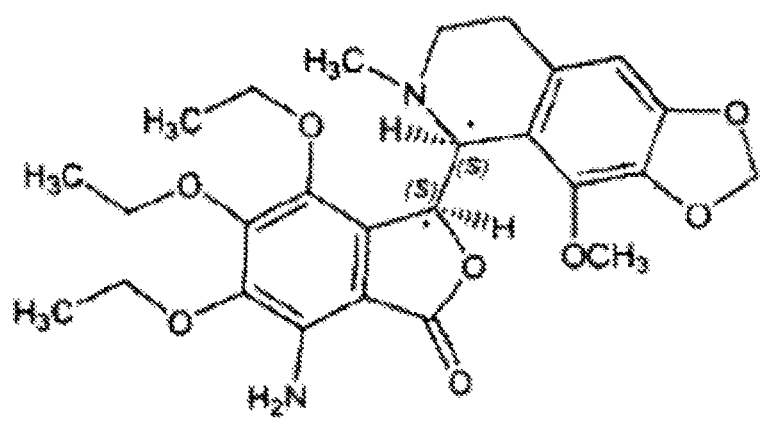
FIG. 4C shows the form of the isomer D2.
Figure 5:
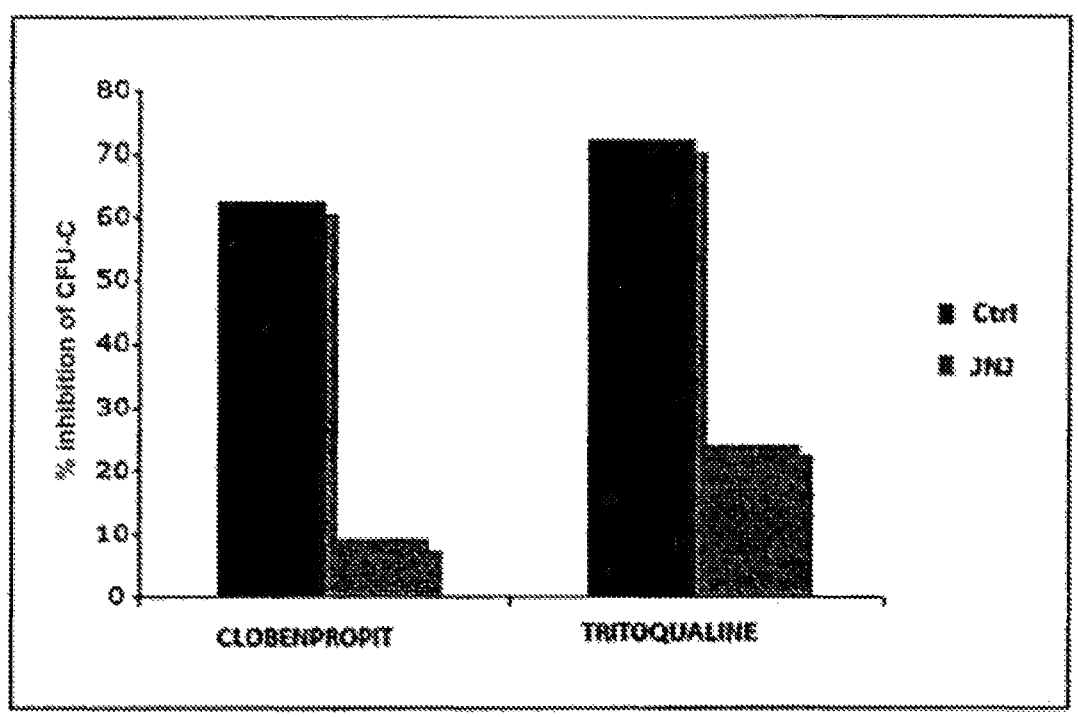
FIG. 5 compares tritoqualine and Clobenpropit, reference H4 agonist. This figure reveals that tritoqualine is able to inhibit the proliferation of CFU rich in H4 receptor. When an anti H4 is used, the activity of tritoqualine is substantially diminished as that of Clobenpropit. This demonstrates well that tritoqualine is an H4 agonist molecule.

FIG. 3B shows the effect of the bleomycin on the lung tissue.

DETAILED DESCRIPTION

Example

Protocol

The bleomycin mouse protocol (BLM) was conducted with all of the mice of each group of 10 mice (species: C57/B16J, referred to further on as BL6); these are female mice 8 weeks old.

The analyse of the Fibrosis was conducted with all the animals of each group, respectively. The extent of the fibrosis was analysed biochemically, histologically and cytologically using various quantitative and semi quantitative methods.

All of the mice BL6 are treated according to the protocol hereinbelow.

5 groups of mice were evaluated.

The treatment with bleomycin (BLM) is done according to the following protocol:

All of the mice of all of the groups (except group 1) receive bleomycin (BLM) intranasally (3 mg/kg via intranasal instillation) for 5 consecutive days and will be monitored daily and killed at D+29 after BLM instillation in order to study the chronic pulmonary inflammation and the fibrosis. The bleomycin being administered five times at the age of 8 weeks (see diagram 3A).

The treatment with tritoqualine is done in 2 doses, 20 and 40 mg/kg/day throughout the entire life of the mice. The treatment with tritoqualine starts fourteen days after the first inhalation of the treatment with bleomycin. The treatment is done orally. The groups studied were as follows:

| | | |
|---|---|---|
| 1. BL6 mice | NaCl | |
| 2. BL6 mice | BLM + vehicle | |
| 3. BL6 mice | BLM + pirfenidone (100 mg/kg, po) | |
| 4. BL6 mice | BLM + tritoqualine (20 mg/kg, po) | |
| 5. BL6 mice | BLM + tritoqualine (40 mg/kg, po) | |

The Histology

After bronchoalveolar lavage (BAL) and perfusion of the lung, the large lobe was fixed in 4% buffered formaldehyde for standard microscopic analysis (Leica microscope). 3-mm sections were coloured with Masson's trichrome (TM) by using standard techniques, which allow for the evaluation of the fibrosis (TM) as the fibres of collagen are coloured blue and the observation of the extent of the inflammation.

The fibrosis was evaluated by a semi-quantitative score (0-5) (Ashcroft score) with the increase in severity by two independent observers.

The fibrosis with the deposit of collagen located at the alveolar walls and in the peribronchial area and the infiltration of inflammatory cells were evaluated using a semi-quantitative score of 0-5 with an increasing severity by two independent observers.

Titration of Collagen (Hydroxyproline)

The collagen content is done after homogenisation of the lung. After bronchoalveolar lavage (BAL), the entire lung was perfused with a saline solution through the right ventricle of the heart in order to empty the vascular content.

The lungs were frozen at −70° C. until they were used. The lung was then homogenised in PBS and centrifuged.

The supernatant was discarded and the lower portion was put back into suspension in 1 ml of PBS containing 0.5% hexadecyltrimethylammonium bromide (HTAB) and 5 mM ethylene-diamine-tetra-acetic acid (EDTA).

After centrifugation, the collagen content was determined by the Sircol assay (France Biochem Division, France), as described by the manufacturer.

The Measurement of Cytokines

The interferon gamma and TGFβ levels were measured in a lung homogenate; the concentrations of these different cytokines were determined by a Luminex assay using a MAGPIX (Biorad, France) according to the manufacturer's instructions.

The Results

The histological measurements according to the method evaluated by a semi-quantitative score (0-5) (Ashcroft score) gives the following results:

Pirfenidone test 100 mg/kg versus bleomycin for the histology.

Paired t test (Student test)

P value 0, 0449

P value summary: The P<0.05 Is the test significant? Yes

Is the test highly significant? No, the difference is low (P=0.045) at the limit of significance.

Mean±standard deviation (bleomycin): 4.2±0.14, n=10

Mean±standard deviation (Pirfenidone): 3.8±0.12 n=10

Difference between the two means: −0.40±0.18

Conclusion: efficacy of pirfenidone at the limit of significance.

Tritoqualine test 20 mg/kg versus bleomycin for the histology.

Paired t test (Student test)

P value<0, 0002

P value summary: The P<0.0002 Is the test significant? Yes

Is the test highly significant? Yes, the difference is very high (P=0.0002) very high significance. See FIG. 2A.

Conclusion: very high efficacy of tritoqualine with a high significance

Tritoqualine whether at the dose of 20 or 40 mg/kg substantially decreases the histological score and this is highly significant. Pirfenidone is at the limit of significance (P 0.045)) while for tritoqualine the difference is highly significant (P=0.0001 for the dose of 20 mg/kg)—See FIG. 2B.

The titration of the collagen (method by the dosage of hydroxyproline) is expressed in μg/mg of proteins.

Pirfenidone test 100 mg/kg versus bleomycin for the collagen (hydroxyproline).

Unpaired t test (Student test)

P value 0, 0450

P value summary: The P<0.05 Is the test significant? Yes

Is the test highly significant? No, the difference is low (P=0.045) at the limit of significance.

Mean±standard deviation (bleomycin): 340.0±4.888, n=10

Mean±standard deviation (Pirfenidone): 316.5±9.748, n=10

Difference between the two means: −23.50±10.90

Conclusion: efficacy of pirfenidone at the limit of significance (P 045).

Tritoqualine test 20 mg/kg versus bleomycin for the collagen (hydroxyproline).

Unpaired t test (Student test)

P value<0, 0001

P value summary: The P<0.0001 Is the test significant? Yes

Is the test highly significant? Yes, the difference is very high (P=0.0001) very high significance.

Mean±standard deviation (bleomycin): 340.0±4.888, n=10

Mean±standard deviation (Trito 20 mg/kg): 280.0±7.528, n=10

Difference between the two means: −60.00±8.975

Conclusion: very high efficacy of tritoqualine with a high significance.

Tritoqualine has a strong action on the inhibition of the formation of collagen which is much higher than that of pirfenidone. The significance is also substantial (P=0, 0001)—See FIG. 2A.

The dosage of cytokines: Tritoqualine also strongly inhibits the TGFβ. (P=0.001) as with pirfenidone (P=0.001) see FIG. 1A.

Tritoqualine could be used in different forms, outside of its "tablet" form without modifying its efficacy, for example in the form of a soft capsule, syrup, oral gel, capsule or tablet with programmed disintegration.

Tritoqualine has already been used in humans at a dose of 3 mg/kg, but never in idiopathic pulmonary fibrosis, however this dose should be active in humans in this pathology.

Indeed the doses used in animals are in general 10 times higher than the doses used in humans. Esbriet is for example used at a dose of 100 mg/kg in mice while in humans the dose used is only 15 mg/kg.

This dose ratio is without a doubt the same for tritoqualine. The doses that could be effective would then be from 3 to 40 mg/kg.

The invention claimed is:

1. A method of treating idiopathic pulmonary fibrosis in a subject in need thereof, comprising:
   administering to said subject a therapeutically effective amount of a substance having an agonist activity on the histamine H4 receptor,
   wherein the substance is comprised of an isomer or of a mixture of isomers of tritoqualine.

2. The method according to claim 1, wherein the substance is administered in a dosage form selected from soft capsules, tablets, capsules, a syrup, and a gel.

3. The method according to claim 2, wherein the dosage form provides a dose of 3 to 40 mg/kg of the subject.

4. The method according to claim 1, wherein the therapeutically effective amount is 1.4 g to 2.8 g per day.

* * * * *